United States Patent
Wilt et al.

(10) Patent No.: US 9,433,468 B2
(45) Date of Patent: Sep. 6, 2016

(54) SHEATH FOR A MEDICAL OR DENTAL INSTRUMENT

(71) Applicant: TIDI Products, LLC, Neenah, WI (US)

(72) Inventors: Brian L. Wilt, Appleton, WI (US); Kurt Miller, Neenah, WI (US)

(73) Assignee: TIDI Products, LLC, Neenah, WI (US)

( * ) Notice: Subject to any disclaimer, the term of this patent is extended or adjusted under 35 U.S.C. 154(b) by 0 days.

(21) Appl. No.: 14/505,937

(22) Filed: Oct. 3, 2014

(65) Prior Publication Data

US 2015/0100047 A1   Apr. 9, 2015

Related U.S. Application Data

(60) Provisional application No. 61/886,775, filed on Oct. 4, 2013.

(51) Int. Cl.
| | |
|---|---|
| *A61B 19/02* | (2006.01) |
| *A61B 1/00* | (2006.01) |
| *A61B 1/24* | (2006.01) |
| *A61B 5/00* | (2006.01) |

(52) U.S. Cl.
CPC ........... *A61B 19/02* (2013.01); *A61B 1/00144* (2013.01); *A61B 1/24* (2013.01); *A61B 5/0088* (2013.01); *A61C 2202/00* (2013.01)

(58) Field of Classification Search
CPC .. A61B 1/00144; A61B 1/24; A61B 5/0088; A61B 19/02; A61B 19/026; B65D 75/5805; G01K 1/083; A61C 2202/00
USPC ........ 206/305, 306, 320, 363, 364, 368, 438
See application file for complete search history.

(56) References Cited

U.S. PATENT DOCUMENTS

| | | | |
|---|---|---|---|
| 3,028,576 A | 4/1962 | Gerard | |
| 3,190,436 A * | 6/1965 | Diamant | G01K 1/083 206/306 |
| 3,308,940 A * | 3/1967 | Morris, Jr. | G01K 1/083 206/306 |
| 3,752,309 A * | 8/1973 | Hopkins | G01K 1/083 206/306 |
| 3,794,091 A | 2/1974 | Ersek et al. | |

(Continued)

FOREIGN PATENT DOCUMENTS

| | | |
|---|---|---|
| EP | 0477581 | 4/1992 |
| EP | 2229120 | 2/2011 |

(Continued)

OTHER PUBLICATIONS

European Patent Office Search Report for App. No. 14 187 684.7 dated Feb. 19, 2015; 7 pages.

(Continued)

*Primary Examiner* — Bryon Gehman
(74) *Attorney, Agent, or Firm* — Boyle Fredrickson, S.C.

(57) ABSTRACT

A sheath includes a plurality of layers coupled to one another and configured to cover a medical or dental instrument. The sheath may include an instrument cover segment and a cable cover segment attached to each other. When in a pre-use configuration, such as when packaged, the cable cover segment may define an inside-out position and overlie at least a portion of the instrument cover segment. When in an in-use configuration, such as when the sheath is installed over a medical or dental instrument, the cable cover segment may define an outside-out position and extend longitudinally with respect to the instrument cover segment.

18 Claims, 6 Drawing Sheets

(56) References Cited

U.S. PATENT DOCUMENTS

| | | | |
|---|---|---|---|
| 3,809,228 A * | 5/1974 | Fowler | B65D 75/5805 206/306 |
| 3,850,084 A * | 11/1974 | Fowler | B65D 75/5805 206/306 |
| 4,000,029 A | 12/1976 | Michaels | |
| 4,026,751 A * | 5/1977 | Fowler | G01K 1/08 206/306 |
| 4,062,239 A | 12/1977 | Fowler et al. | |
| 4,113,169 A | 9/1978 | Carlisle | |
| 4,161,503 A | 7/1979 | Foulkes et al. | |
| 4,165,000 A * | 8/1979 | Poncy | G01K 1/083 206/306 |
| 4,197,944 A * | 4/1980 | Catlin | G01K 1/083 206/306 |
| 4,552,717 A | 11/1985 | Murley et al. | |
| 4,614,442 A * | 9/1986 | Poncy | G01K 1/083 206/306 |
| 4,646,365 A | 3/1987 | Suprise et al. | |
| 4,662,360 A | 5/1987 | O'Hara et al. | |
| 4,757,381 A | 7/1988 | Cooper et al. | |
| 4,776,921 A | 10/1988 | French | |
| 4,823,949 A | 4/1989 | Bala | |
| 4,825,850 A | 5/1989 | Opie et al. | |
| 4,846,344 A | 7/1989 | Bala | |
| 4,878,486 A * | 11/1989 | Slater | A61B 1/267 206/438 |
| 4,907,395 A | 3/1990 | Opie et al. | |
| 4,942,867 A | 7/1990 | Takahashi et al. | |
| 4,943,406 A | 7/1990 | Bocchi | |
| 4,947,827 A | 8/1990 | Opie et al. | |
| 4,997,092 A * | 3/1991 | Dupont | A61F 13/02 206/363 |
| 5,025,778 A | 6/1991 | Silverstein et al. | |
| 5,069,337 A | 12/1991 | Bala | |
| 5,078,483 A | 1/1992 | Herzberg | |
| 5,107,988 A | 4/1992 | Bala | |
| 5,193,525 A | 3/1993 | Silverstein et al. | |
| 5,228,851 A | 7/1993 | Burton | |
| 5,262,181 A | 11/1993 | Torterotot | |
| 5,274,500 A | 12/1993 | Dunn | |
| 5,325,846 A | 7/1994 | Szabo | |
| 5,328,368 A | 7/1994 | Lansing et al. | |
| 5,337,734 A | 8/1994 | Saab | |
| 5,382,162 A | 1/1995 | Sharp | |
| 5,406,939 A * | 4/1995 | Bala | A61B 1/00142 206/368 |
| 5,433,221 A | 7/1995 | Adair | |
| 5,443,781 A | 8/1995 | Saab | |
| 5,447,148 A | 9/1995 | Oneda et al. | |
| 5,476,090 A | 12/1995 | Kishi | |
| 5,483,951 A | 1/1996 | Frassica et al. | |
| 5,487,376 A | 1/1996 | Yabe et al. | |
| 5,496,259 A | 3/1996 | Perkins | |
| 5,516,010 A | 5/1996 | O'Hara et al. | |
| 5,518,501 A | 5/1996 | Oneda et al. | |
| 5,520,607 A | 5/1996 | Frassica et al. | |
| 5,536,235 A | 7/1996 | Yabe et al. | |
| 5,536,236 A | 7/1996 | Yabe et al. | |
| 5,538,496 A | 7/1996 | Yabe et al. | |
| 5,545,121 A | 8/1996 | Yabe et al. | |
| 5,554,098 A | 9/1996 | Yabe et al. | |
| 5,569,161 A | 10/1996 | Ebling et al. | |
| 5,573,494 A | 11/1996 | Yabe et al. | |
| 5,575,756 A | 11/1996 | Karasawa et al. | |
| 5,591,202 A | 1/1997 | Slater et al. | |
| 5,598,850 A | 2/1997 | Miller et al. | |
| 5,661,851 A | 9/1997 | Sanchez | |
| 5,667,068 A | 9/1997 | Weaver | |
| 5,674,182 A | 10/1997 | Suzuki et al. | |
| 5,685,822 A | 11/1997 | Harhen | |
| 5,685,825 A | 11/1997 | Takase et al. | |
| 5,692,610 A | 12/1997 | Porteous | |
| 5,695,454 A | 12/1997 | Mourkidou | |
| 5,707,342 A | 1/1998 | Tanaka | |
| 5,707,343 A | 1/1998 | O'Hara et al. | |
| 5,707,344 A | 1/1998 | Nakazawa et al. | |
| 5,738,630 A | 4/1998 | Suzuki et al. | |
| 5,743,849 A | 4/1998 | Rice et al. | |
| 5,746,694 A | 5/1998 | Wilk et al. | |
| 5,779,625 A | 7/1998 | Suzuki | |
| 5,795,632 A | 8/1998 | Buchalter | |
| 5,807,107 A | 9/1998 | Bright et al. | |
| 5,827,177 A | 10/1998 | Oneda et al. | |
| 5,830,146 A | 11/1998 | Skladnev | |
| 5,848,895 A | 12/1998 | Martin et al. | |
| 5,863,287 A | 1/1999 | Segawa | |
| 5,865,621 A | 2/1999 | Calderwood | |
| 5,876,328 A | 3/1999 | Fox et al. | |
| 5,876,329 A | 3/1999 | Harhen | |
| 5,893,712 A | 4/1999 | Stone et al. | |
| 5,910,104 A | 6/1999 | Dobak et al. | |
| 5,915,963 A | 6/1999 | Homra | |
| 5,916,145 A | 6/1999 | Chu et al. | |
| 5,921,776 A | 7/1999 | Heilbrunn | |
| 5,924,977 A | 7/1999 | Yabe et al. | |
| 5,927,974 A | 7/1999 | Homra | |
| 5,930,836 A | 8/1999 | Morris | |
| 5,935,058 A | 8/1999 | Makita et al. | |
| 5,938,586 A | 8/1999 | Wilk | |
| D417,273 S | 11/1999 | Walker | |
| 5,980,450 A | 11/1999 | Thompson | |
| 5,980,451 A | 11/1999 | O'Hara | |
| 6,051,293 A | 4/2000 | Weilandt | |
| 6,077,074 A | 6/2000 | Homra | |
| 6,086,530 A | 7/2000 | Mack | |
| 6,095,811 A | 8/2000 | Stearns | |
| 6,096,065 A | 8/2000 | Crowley | |
| 6,146,389 A | 11/2000 | Geitz | |
| 6,174,280 B1 | 1/2001 | Oneda et al. | |
| 6,213,123 B1 | 4/2001 | Miller et al. | |
| 6,224,256 B1 | 5/2001 | Bala | |
| 6,224,543 B1 | 5/2001 | Gammons et al. | |
| 6,270,494 B1 | 8/2001 | Kovalcheck et al. | |
| 6,282,442 B1 | 8/2001 | DeStefano et al. | |
| 6,293,907 B1 | 9/2001 | Axon et al. | |
| 6,293,909 B1 | 9/2001 | Chu et al. | |
| 6,293,952 B1 | 9/2001 | Brosens et al. | |
| 6,305,536 B1 | 10/2001 | Tanaka | |
| 6,346,073 B1 | 2/2002 | Thompson | |
| 6,350,231 B1 | 2/2002 | Ailinger et al. | |
| 6,350,232 B1 | 2/2002 | Hascoet et al. | |
| 6,383,209 B1 | 5/2002 | Crowley | |
| 6,385,484 B2 | 5/2002 | Nordstrom et al. | |
| 6,390,671 B1 | 5/2002 | Tseng | |
| 6,402,511 B1 | 6/2002 | Calderwood | |
| 6,411,838 B1 | 6/2002 | Nordstrom et al. | |
| 6,428,470 B1 | 8/2002 | Thompson | |
| 6,454,702 B1 | 9/2002 | Smith | |
| 6,458,075 B1 | 10/2002 | Sugiyama et al. | |
| 6,461,294 B1 | 10/2002 | Oneda et al. | |
| 6,478,730 B1 | 11/2002 | Bala et al. | |
| 6,500,142 B1 | 12/2002 | Harreld et al. | |
| 6,514,075 B1 | 2/2003 | Jacob | |
| 6,517,539 B1 | 2/2003 | Smith et al. | |
| 6,520,214 B1 | 2/2003 | Sugiyama et al. | |
| 6,530,881 B1 | 3/2003 | Ailinger et al. | |
| 6,537,205 B1 | 3/2003 | Smith | |
| 6,537,207 B1 | 3/2003 | Rice et al. | |
| 6,540,669 B2 | 4/2003 | Abe et al. | |
| 6,549,794 B1 | 4/2003 | Nadeau et al. | |
| 6,551,238 B2 | 4/2003 | Staud | |
| 6,551,239 B2 | 4/2003 | Renner et al. | |
| 6,579,582 B1 | 6/2003 | Harhen et al. | |
| 6,589,164 B1 | 7/2003 | Flaherty | |
| 6,599,239 B2 | 7/2003 | Hayakawa et al. | |
| 6,616,601 B2 | 9/2003 | Hayawaka et al. | |
| 6,623,424 B2 | 9/2003 | Hayakawa et al. | |
| 6,692,251 B1 | 2/2004 | Logan et al. | |
| 6,733,440 B2 | 5/2004 | Ailinger et al. | |
| 6,740,030 B2 | 5/2004 | Martone et al. | |
| 6,743,206 B1 | 6/2004 | Smith et al. | |
| 6,749,601 B2 | 6/2004 | Chin | |
| 6,760,613 B2 | 7/2004 | Nordstrom et al. | |
| 6,761,717 B2 | 7/2004 | Bales et al. | |

(56) References Cited

U.S. PATENT DOCUMENTS

| | | | |
|---|---|---|---|
| 6,768,918 B2 | 7/2004 | Zelenchuk | |
| 6,783,362 B2 | 8/2004 | Cao | |
| 6,793,661 B2 | 9/2004 | Hamilton et al. | |
| 6,818,903 B2 | 11/2004 | Schomacker et al. | |
| 6,826,422 B1 | 11/2004 | Modell et al. | |
| D500,134 S | 12/2004 | Banks et al. | |
| 6,839,661 B2 | 1/2005 | Costa et al. | |
| 6,840,900 B2 | 1/2005 | Smith | |
| 6,847,490 B1 | 1/2005 | Nordstrom et al. | |
| 6,878,107 B2 | 4/2005 | Hino | |
| 6,881,186 B2 | 4/2005 | Smith | |
| 6,889,069 B2 | 5/2005 | Routt et al. | |
| 6,895,264 B2 | 5/2005 | Rice et al. | |
| 6,902,935 B2 | 6/2005 | Kaufman et al. | |
| 6,908,428 B2 | 6/2005 | Aizenfeld et al. | |
| D507,349 S | 7/2005 | Banks et al. | |
| 6,933,154 B2 | 8/2005 | Schomacker et al. | |
| 6,939,293 B2 | 9/2005 | Conteas | |
| 6,971,875 B2 | 12/2005 | Cao | |
| 6,972,017 B2 | 12/2005 | Smith et al. | |
| 7,025,923 B2 | 4/2006 | Harhen et al. | |
| 7,029,436 B2 | 4/2006 | Lizuka et al. | |
| 7,033,315 B2 | 4/2006 | Smith | |
| 7,037,110 B1 | 5/2006 | Hale | |
| 7,044,906 B2 | 5/2006 | Hosoi et al. | |
| 7,052,495 B2 | 5/2006 | Smith | |
| 7,056,284 B2 | 6/2006 | Martone et al. | |
| 7,066,733 B2 | 6/2006 | Logan et al. | |
| 7,070,559 B2 | 7/2006 | Adams et al. | |
| 7,081,097 B2 | 7/2006 | Mortone et al. | |
| 7,086,858 B2 | 8/2006 | Cao | |
| 7,094,054 B2 | 8/2006 | Cao | |
| 7,103,401 B2 | 9/2006 | Schomacker et al. | |
| 7,127,282 B2 | 10/2006 | Nordstrom et al. | |
| 7,136,518 B2 | 11/2006 | Griffin et al. | |
| 7,157,502 B2 | 1/2007 | Stannard | |
| 7,187,810 B2 | 3/2007 | Clune et al. | |
| 7,226,411 B2 | 6/2007 | Akiba | |
| 7,260,248 B2 | 8/2007 | Kaufman et al. | |
| 7,276,067 B2 | 10/2007 | Bales et al. | |
| 7,282,723 B2 | 10/2007 | Schomacker et al. | |
| 7,292,895 B2 | 11/2007 | Benhalima et al. | |
| 7,309,867 B2 | 12/2007 | Costa et al. | |
| 7,310,547 B2 | 12/2007 | Zelenchuk | |
| 7,311,441 B2 * | 12/2007 | Weaver | G06F 3/039 206/320 |
| 7,341,564 B2 | 3/2008 | Zwiefel et al. | |
| 7,357,788 B2 | 4/2008 | Gammons | |
| 7,413,542 B2 | 8/2008 | Kucklick et al. | |
| 7,435,214 B2 | 10/2008 | Kucklick et al. | |
| 7,459,696 B2 | 12/2008 | Schomacker et al. | |
| 7,469,160 B2 | 12/2008 | Banks et al. | |
| 7,488,298 B2 | 2/2009 | Patel et al. | |
| 7,511,733 B2 | 3/2009 | Takizawa et al. | |
| 7,520,950 B2 | 4/2009 | Saadat et al. | |
| 7,645,230 B2 | 1/2010 | Mikkaichi et al. | |
| 7,665,893 B2 | 2/2010 | Buchalter | |
| 7,718,125 B2 | 5/2010 | Bala | |
| 7,740,802 B2 | 6/2010 | Bala | |
| 7,762,949 B2 | 7/2010 | Nakao | |
| 7,790,105 B2 | 9/2010 | Bala | |
| 7,803,109 B2 | 9/2010 | Gomez | |
| 7,811,516 B2 | 10/2010 | Bala | |
| 7,850,006 B2 | 12/2010 | Uchiyama | |
| 7,905,830 B2 | 3/2011 | Stefanchik et al. | |
| 7,918,783 B2 | 4/2011 | Maseda et al. | |
| 7,951,072 B2 | 5/2011 | Adams et al. | |
| 7,998,061 B2 | 8/2011 | Kucklick et al. | |
| 8,012,083 B2 | 9/2011 | Kucklick et al. | |
| 8,092,374 B2 | 1/2012 | Smith et al. | |
| 8,092,481 B2 | 1/2012 | Nance et al. | |
| 8,142,347 B2 | 3/2012 | Griego et al. | |
| 8,162,938 B2 | 4/2012 | Smith et al. | |
| 8,167,790 B2 | 5/2012 | Kucklick et al. | |
| 8,241,280 B2 | 8/2012 | Bales et al. | |
| 8,353,819 B2 | 1/2013 | Okoniewski | |
| 8,360,968 B2 | 1/2013 | Hadani | |
| 8,444,551 B2 | 5/2013 | Adams et al. | |
| 8,454,501 B2 | 6/2013 | Fernandez et al. | |
| 8,506,578 B2 | 8/2013 | Smith | |
| 8,663,090 B2 | 3/2014 | Fujimoto | |
| 8,663,159 B2 | 3/2014 | Gorini et al. | |
| 8,690,764 B2 | 4/2014 | Clark et al. | |
| 8,696,550 B2 | 4/2014 | Surti | |
| 9,151,313 B2 | 10/2015 | Frank | |
| 2002/0013511 A1 | 1/2002 | Ailinger et al. | |
| 2002/0128538 A1 | 9/2002 | Thompson | |
| 2005/0049460 A1 | 3/2005 | Mikkaichi et al. | |
| 2005/0143625 A1 | 6/2005 | Whitmore | |
| 2005/0177025 A1 | 8/2005 | Jaker et al. | |
| 2005/0181327 A1 | 8/2005 | Graham et al. | |
| 2005/0222581 A1 | 10/2005 | Fischer | |
| 2005/0234295 A1 | 10/2005 | Gomez | |
| 2006/0258907 A1 | 11/2006 | Stefanchik et al. | |
| 2006/0258908 A1 | 11/2006 | Stefanchik et al. | |
| 2007/0073107 A1 | 3/2007 | Peatree et al. | |
| 2007/0185383 A1 | 8/2007 | Mulhern et al. | |
| 2007/0259307 A1 | 11/2007 | Quan et al. | |
| 2008/0228029 A1 | 9/2008 | Mikkaichi et al. | |
| 2008/0228035 A1 | 9/2008 | Hagigara et al. | |
| 2009/0069631 A1 | 3/2009 | Ogura | |
| 2009/0112066 A1 | 4/2009 | Yago et al. | |
| 2009/0253962 A1 | 10/2009 | Fernandez et al. | |
| 2009/0318764 A1 | 12/2009 | Yoshimoto | |
| 2010/0063358 A1 | 3/2010 | Kessler | |
| 2010/0145150 A1 | 6/2010 | Fukunaga | |
| 2010/0174144 A1 | 7/2010 | Hsu et al. | |
| 2011/0087070 A1 | 4/2011 | Tilson et al. | |
| 2011/0282152 A1 | 11/2011 | Cant | |
| 2012/0071721 A1 | 3/2012 | Remijan et al. | |
| 2012/0143006 A1 | 6/2012 | Avitsian et al. | |
| 2012/0273994 A1 | 11/2012 | Yoshimoto | |
| 2012/0316391 A1 | 12/2012 | Weitzner et al. | |
| 2013/0053644 A1 | 2/2013 | Smith et al. | |
| 2013/0267778 A1 | 10/2013 | Rehe | |
| 2013/0345515 A1 | 12/2013 | Fitzmaurice | |
| 2014/0005480 A1 | 1/2014 | Wagner et al. | |
| 2014/0046343 A1 | 2/2014 | Okazaki et al. | |

FOREIGN PATENT DOCUMENTS

| | | |
|---|---|---|
| GB | 1053955 | 1/1967 |
| WO | WO0041615 | 7/2000 |
| WO | WO 2009/077176 | 6/2009 |
| WO | WO2010103501 | 9/2010 |

OTHER PUBLICATIONS

"Elipar TM S10" Technical Data Sheet; 3m ESPE; 2010 [retrieved Jul. 21, 2014]. Retrieved from the Internet <http://multimedia.3m.com/mws/media/578770/elipartm-s10-led-curing-light.pdf?fn=elipar_s10_tds.pdf>.

* cited by examiner

SHEATH FOR A MEDICAL OR DENTAL INSTRUMENT

CROSS-REFERENCE TO RELATED APPLICATION

This application claims the benefit of priority based on Provisional Patent Application No. 61/886,775, filed Oct. 4, 2013, the entire contents of which are hereby expressly incorporated by reference into the present application.

BACKGROUND OF THE INVENTION

1. Field of the Invention

The invention generally relates to sheaths, coverings, and barriers for instruments such as probes, cameras, and/or other devices used in medical or dental procedures.

2. Discussion of the Related Art

A number of different types of instruments are utilized in a variety of medical and dental settings. Such instruments typically employ a removable protective sleeve, sheath, cover, or barrier to prevent cross-contamination. Many of these removable protectable sleeves, sheaths, covers, or barriers enclose portions of the instruments that are gripped by the caregivers and engage patients while leaving other portions of the instruments and/or portions of cables or tubes extending from the instruments exposed.

SUMMARY OF THE INVENTION

The present invention provides a sheath that is stored in a compact manner and can be easily deployed to cover an entire instrument for use in a medical or dental procedure and a portion of a cable or tube extending from the instrument. The sheath defines a folded pre-use configuration and an unfolded in-use configuration. The sheath may include a single fold arrangement having an inverted outer layer such as a continuous tubular cable cover segment that can be pulled over the instrument and onto a cable or tube of the instrument. The inverted outer layer may define a pair of inverted flaps that can be unfolded and attached to each other to define a continuous tubular cable cover segment. These arrangements may allow individual sheaths to be packaged compactly for easy storage and manipulation in the pre-use configuration while allowing the sheaths to cover not only the instruments, but also cover at least portions of cables or tubes of the instruments. This may prevent cross-contamination by providing barriers over relatively larger surface areas of the instruments and corresponding cables or tubes. This also facilitates easy installation of relatively long sheaths over the instruments and corresponding cables or tubes by avoiding the frictional resistance associated with sliding these relatively long sheaths sequentially over instruments and their cables or tubes.

In accordance with one aspect of the invention, a sheath may be installed upon an instrument by inserting a tip of an instrument into a pocket of an instrument cover segment of a sheath toward a tip end of the instrument cover segment. Optionally, a tab may be provided and grasped and which is arranged between the instrument cover segment and a cable cover segment of the sheath. The tab may be arranged toward a tip end of the instrument cover segment and the cable cover may define an inside-out position and overlie at least a portion of the instrument cover segment. The tab may he pulled away from the tip end of the instrument cover. The cable cover segment may be inverted from an inside-out position to define an outside-out position in which the cable cover segment extends longitudinally away from the instrument cover segment and overlies at least a portion of a length of cable or tube of the instrument. The tab may be released from the sheath.

In accordance with another aspect of the invention, a pair of flaps may be moved from a folded position in which the flaps overlie the instrument cover segment to an unfolded position in which the flaps extend longitudinally from the instrument cover segment. The flaps may be secured to each other on opposing sides of at least a portion of a length of cable or tube of the instrument so as to provide a continuous barrier extending the entire length of the instrument and over at least a portion of the cable or tube.

According to another aspect of the invention, the sheath may include an instrument cover segment and a cable cover segment. The instrument and cable cover segments of the sheath may be arranged with respect to each other so that when the sheath is in the pre-use configuration, the cable cover segment defines an inside-out position and overlies at least a portion of the instrument cover segment. When the sheath is in the in-use configuration, the cable cover segment may define an outside-out position and extend longitudinally with respect to the instrument cover segment.

According to another aspect of the invention, the instrument cover segment may include a tip end receiving a tip of the instrument and an opposite outer end. The cable cover segment may define an inner end connected to the outer end of the instrument cover segment. The cable cover segment may define an outer end arranged relatively closer to the tip end of the instrument cover segment when the sheath is in the pre-use configuration and relatively further from the tip end of the instrument cover segment when the sheath is in the in-use configuration. The outer end of the cable cover segment may travel longitudinally past and concentrically outward of the inner end of the cable cover segment while the cable cover segment inverts during an installation of the sheath upon the instrument.

According to another aspect of the invention, a fold may be defined between the instrument and cable cover segments when the sheath is in the pre-use configuration. The sheath in the pre-use configuration may define multiple layers, including a sleeve layer having a pocket for receiving an instrument and an outer layer arranged outwardly of and covering the sleeve layer.

According to another aspect of the invention, a tab may be arranged between the sleeve layer and the outer layer for pulling the outer layer away from the sleeve layer. The tab may define a paper layer arranged between the outer and sleeve layers. Pulling the tab toward the fold may invert the cable cover segment from the inside-out position to the outside-out position during an installation of the sheath upon the instrument. During installation of the sheath upon the instrument, the fold may travel along the length of the cable cover segment toward an open end of the cable cover segment such that the cable cover segment inverts during an installation of the sheath upon the instrument by unrolling the cable cover over the instrument and onto a cable or tube of the instrument.

According to another aspect of the invention, when the sheath is in the pre-use configuration, the outer layer may include a pair of flaps folded over the instrument cover segment. Each of the flaps of the outer layer may be connected to the sleeve layer by a weld. A fold may be defined between the instrument cover segment and each of the flaps of the cable cover segment when the sheath is in the pre-use configuration. At least one of the flaps may include an adhesive layer facing inwardly when the sheath is in the in-use configuration for adhering to the respective other flap for sealing the flaps to each other around an entire perimeter of a cable or tube of the instrument. The adhesive may be arranged at both sides, toward respective edges, of one or both of the flaps.

In accordance with a first aspect of the invention, a sheath includes a plurality of layers coupled to one another and configured to cover a medical or dental instrument. The sheath includes an outer layer, a paper layer, and a sleeve layer. The sleeve layer is configured to be received over a probe end of the instrument while the outer layer is folded or sealed in an inside out manner relative to the sleeve layer and is configured to be pulled over the cable or tubing end of the instrument. The paper layer is removable from the sleeve layer after application of the sheath to the instrument.

In accordance with another aspect of the invention, a sheath including multiple folds is configured to cover a dental or medical instrument. The sheath includes an outer layer, a paper layer and a sleeve layer. The paper layer is adhered to the other layers by way of an adhesive and a number of welds. The paper layer may include a perforated tab to enable easy removal of the paper layer from the sleeve and outer layers.

In yet another aspect of the invention, a method of covering a medical or dental instrument is provided. The method comprises inserting a sleeve layer over a probe end of the medical or dental instrument. Next, an outer layer, which is folded over itself relative to the sleeve layer and attached thereto, is pulled down away from the probe end of the instrument and toward the cabling or tubing thereof to cover the cabling and tubing. Finally, a paper layer is removed from the outer layer by peeling the paper layer away from the outer layer such that the seals or welds therebetween are broken.

Various other features, embodiments, and alternatives of the present invention will be made apparent from the following detailed description taken together with the drawings. It should be understood, however, that the detailed description and specific examples, while indicating preferred embodiments of the invention, are given by way of illustration and not limitation. Many changes and modifications could be made within the scope of the present invention without departing from the spirit thereof, and the invention includes all such modifications.

BRIEF DESCRIPTION OF THE DRAWINGS

Preferred exemplary embodiments of the invention are illustrated in the accompanying drawings, in which like reference numerals represent like parts throughout, and in which.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the words "connected", "attached", or terms similar thereto are often used. They are not limited to direct connection but include connection through other elements where such connection is recognized as being equivalent by those skilled in the art.

DETAILED DESCRIPTION OF THE EMBODIMENTS

Figure 1:
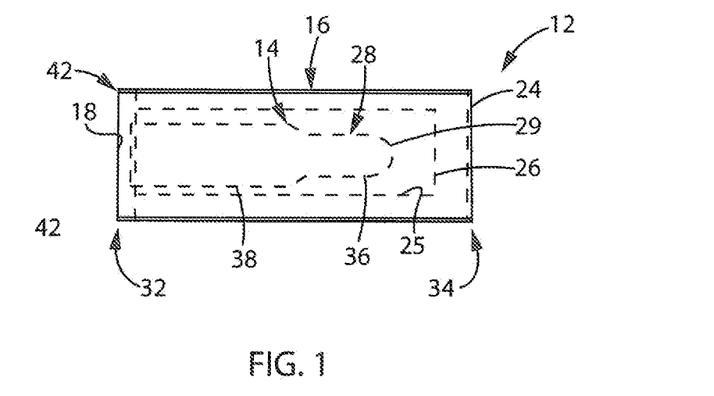
FIG. 1 is a top plan view of a sheath constructed in accordance with a first embodiment of the present invention.
Figure 2:
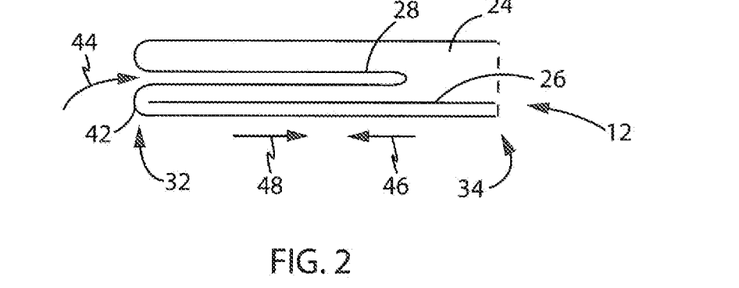
FIG. 2 is a side elevation view of the sheath of FIG. 1.
Figure 3:
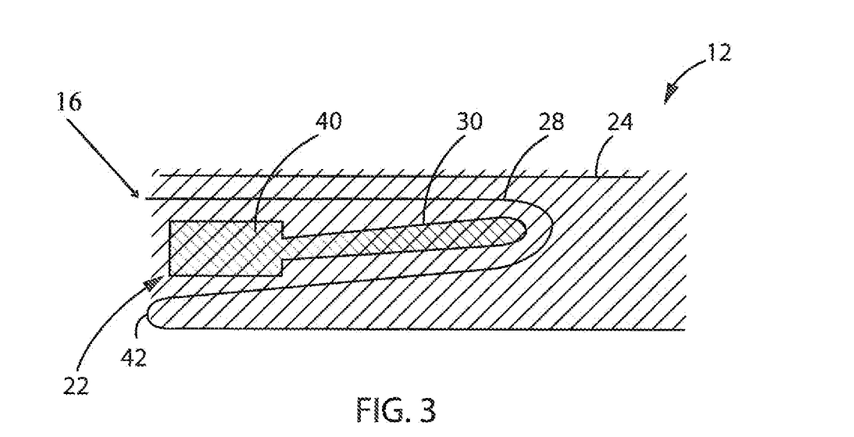
FIG. 3 is a side elevation view of the sheath of FIG. 1 covering an instrument and having a paper layer removed.

Referring to FIGS. 1-3, a sheath 12 includes an instrument cover segment 14 and a cable cover segment 16 connected to each other at respective outer and inner ends at a location shown as fold 18 in FIG. 1. The sheath 12 is configured for covering a medical or dental instrument 22 (see FIG. 3). As shown in FIG. 1, the sheath 12 is provided in its initial, uncovered position to define a pre-use configuration of the sheath 12 in which the cable cover segment 16 is in an inside-out position and overlies at least a portion of the instrument cover segment 14, shown here as overlying the entire instrument cover segment 14. In this pre-use configuration, the sheath 12 has not yet been applied to the instrument 22 and defines a plurality of layers. The layers include an outer layer 24 defined by the cable cover segment 16, a tab 25 that may be defined by a paper layer 26, and a sleeve layer 28 defined by the instrument cover segment 14, which is configured to be used for covering the instrument 22, as will be explained in additional detail hereinafter. The outer layer 24 and the sleeve layer 28 may be constructed from a film or plastic material such as, e.g., polyethylene, polypropylene, or any other suitable polymeric material. The sleeve layer 28 is generally tubular and configured to be received over a tip 30 (see FIG. 3) of the instrument 22 which may include a probe, lens, or sensor. As illustrated, the sleeve layer 28 has a generally tapered shape extending from a first end 32 that defines an outer end of the instrument cover segment 14 to an opposing second end 34 that defines a tip end of the instrument cover segment 14. In particular, the sleeve layer 28 defines a pocket 29 that includes a narrow probe receiving end 36 for receiving the tip 30 of the instrument 22, which may have a rounded end or similar such construction, The probe receiving end 36 extends toward the first end 32 toward a wide control receiving end 38, which may be configured to be received over a control element 40 (see FIG. 3) of the instrument 22. As will be explained in greater detail herein, the outer layer 24 is folded in an inside-out manner relative to the sleeve layer 28 and is configured to be securely received over a cable or tube (not shown) of the instrument 22.

The paper layer 26 may be loosely held between the outer and sleeve layers 24, 28 or may be bonded to at least one of and selectively separable from the outer layer 24 and sleeve layer 28 in a manner that will be described hereinafter. In one embodiment, the paper layer 26 is separably coupled to the outer layer 24 and the sleeve layer 28 by way of a number of seals 42 or folds. The seals 42 may be formed in any conventional manner generally known in the art.

With additional reference now to FIGS. 2 and 3, the sheath 12 is shown in the initial, uncovered position. In the initial, uncovered position, the outer layer 24 is disposed in an inside-out manner relative to the sleeve layer 28, as previously described. To apply the sheath 12 to the instrument 22, the operator of the sheath 12 first inserts the tip 30 of the instrument 22 into the sleeve layer 28 such that the probe receiving end 36 is received over the tip 30 in a direction indicated by arrow 44. The sleeve layer 28 is pulled over the tip 30 until the control receiving end 38 covers the control element 40 of the instrument 22. Next, the outer layer 24 is pulled back over itself in a direction indicated by arrow 46. This may be done by grasping the probe receiving end of the tab 25 and pulling the outer layer 24 down thereby inverting the outer layer 24 with respect to the pre-use configuration. Alternatively, the user may hold the cable and pull the outer layer down over the cable to thereby invert the layers. In so doing, the cable cover segment 16 may be inverted from an inside-out position to define an outside-out position in which the cable cover segment 16 extends longitudinally away from the instrument cover segment 14 and overlies at least a portion of a length of cable or tube of the instrument 22. This enables the outer layer 24 to be pulled over the cable or tube of the instrument 22 as previously indicated. Once the outer layer 24 and, thus, cable cover segment 16 have been pulled over the cable or tube of the instrument 22, the paper layer 26 is exposed and presented to the operator for removal thereof. In particular, the paper layer 26 may be pulled in a direction indicated by arrow 48 such that the seals 42 between the paper layer 26 and the outer layer 24 and sleeve layer 28 are broken such that the paper layer 26 and tab 25 may be removed and disposed of.

Figure 4:
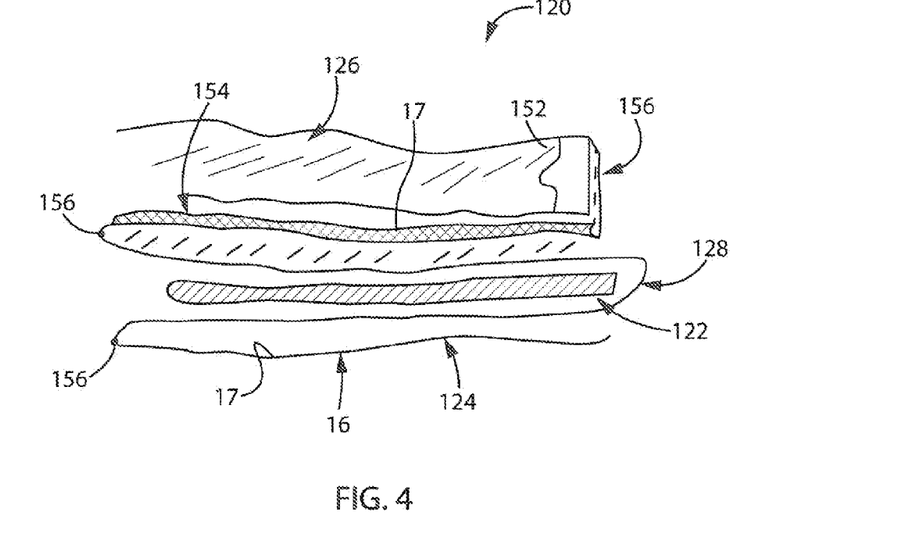
FIG. 4 is an isometric view of a sheath constructed in accordance with a second embodiment of the present invention.
Figure 5:
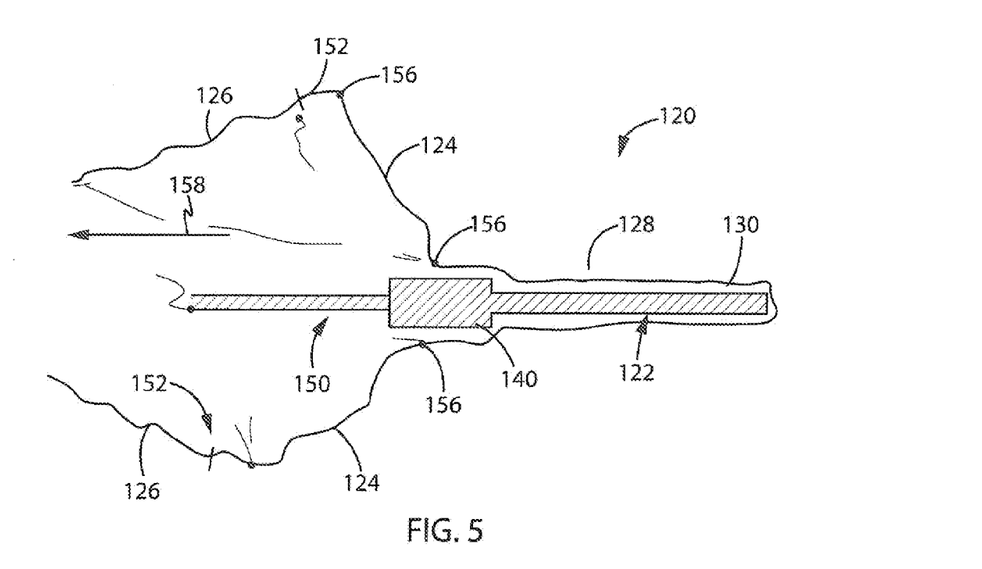
FIG. 5 is a side elevation view of the sheath of FIG. 4 covering an instrument.
Figure 6:
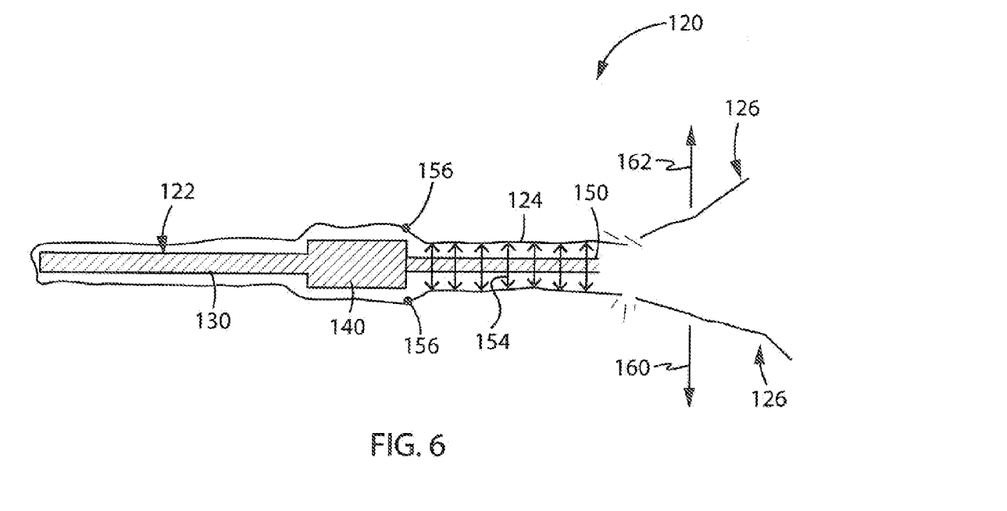
FIG. 6 is a side elevation view of the sheath of FIG. 4 covering the instrument with a paper layer removed therefrom and showing an outer layer adhered together to cover a cable of the instrument.

Turning now to FIGS. 4-6, an alternative construction of the sheath 120 is provided in which the sheath 120 includes multiple folds, welds, or seals 156 for coupling the outer layer 124, paper layer 126, and sleeve layer 128 to one another. In this embodiment, the cable cover segment 16 includes a pair of flaps 17 that define a folded position in which the flaps 17 overlie the instrument cover segment 14 in a pre-use configuration to an unfolded position in which the flaps 17 extend longitudinally from the instrument cover 14 in an in-use configuration. In the present construction, the paper layer 126 is applied to each of the folded over outer layers 124 such that a multiple fold sheath construction is provided. As partly shown in FIG. 4, and also in FIG. 5, the sheath 120 is pulled over a medical or dental instrument 122 (having segments 130 and 140) in much the same manner previously described herein while the layers 124, 126, and 128 are in their initial folded positions prior to being unfolded for capturing the cabling or tubing 150 (see FIG. 5) of the instrument 122.

The outer layer 124, as in the previous embodiment, is folded back over itself and is configured to be pulled over the tubing 150 of the instrument 122, as desired. The paper layer 126 is likewise provided in much the same manner and configured for selective removal once the sheath 120 has been deployed. In this construction, the paper layer 126 may employ a perforated tab 152 for assisting the operator in removing the paper layer 126. The paper layer 126 may be adhered to the sleeve layer 128 by way of an adhesive layer 154 applied along both sides thereof In addition, the paper layer 126 may include a number of heat welds 156 configured to couple the paper layer 128 to the outer layer 124. As will be described herein, the heat welds 156 may be selectively broken by the operator for removing the paper layer 126 as desired.

With additional reference now to FIG. 5, the sheath 120 is shown in an intermediate position in which the outer layer 124 and connected paper layer 126 have been partially pulled back over the instrument 122 in a direction indicated by arrow 158. In particular, the outer layer 124 has been pulled toward the tubing 150 for covering thereof. As the outer layer 124 is pulled back over the tubing 150, the paper layer 126 is exposed for subsequent removal thereof.

With additional reference now to FIG. 6, the sheath 120 is shown with the paper layer 126 broken away from the outer layer 124. As shown in FIG. 6, the outer layer 124 has been pulled down over the tubing 150 of the instrument 122 to provide a covering thereover. The adhesive layer 154 may allow for "zip" seal-type attachment of the flaps 17 to each other to extend over the tubing 150 by progressively adhering along the length of the flaps 17 while the paper layer(s) 126 is being removed by peeling from the respective inner surface(s) of the flap(s) 17. In at least one construction of the invention, a portion of the paper layer 126, such as the perforated tab 152, may remain behind after removal of the paper layer 126 to assist the operator in removing the sheath 12 from the instrument 122. To remove the paper layer 126 from the outer layer 124, the paper layer 126 is pulled away from the outer layer 124 in a direction indicated by arrows 160 and 162.

Figure 7:
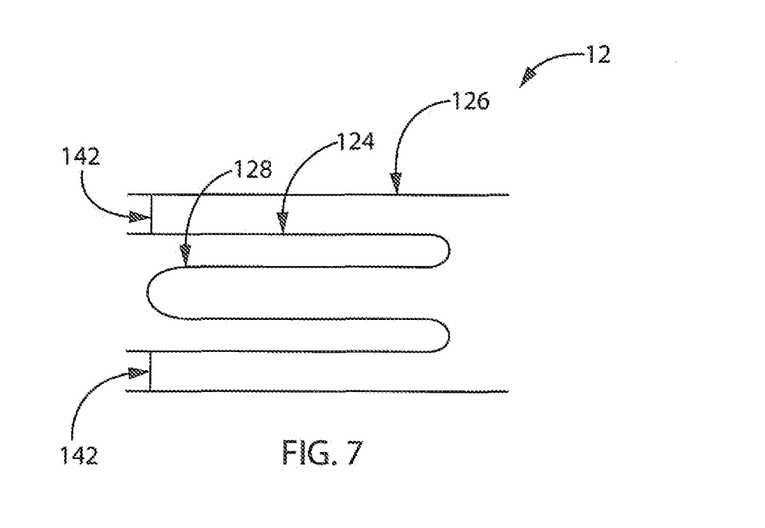
FIG. 7 is a side elevation view of a sheath like the sheath of FIG. 4 according to one construction thereof.
Figure 8:
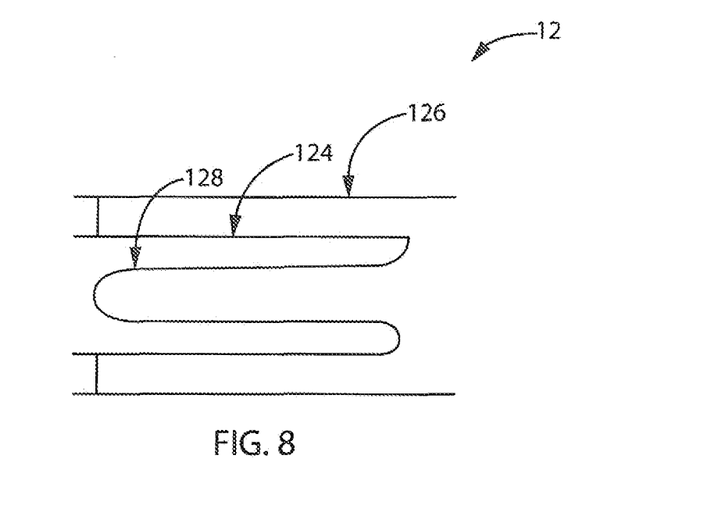
FIG. 8 is a side elevation view of a sheath like the sheath of FIG. 4 according to another construction thereof.

With additional reference now to FIG. 7, the sheath 120 is shown according to a first construction in which the outer layer 124 and the paper layer 126 are coupled to one another by welds 142. As previously described, when the outer layer 124 is pulled over the cable of the instrument, the welds 142 may be broken to separate the paper layer 126 from the outer layer 124. Now with additional reference to FIG. 8, the sheath 120 is shown according to another construction in which the paper layer 126 and outer layer 124 are not coupled to one another.

Figure 9:
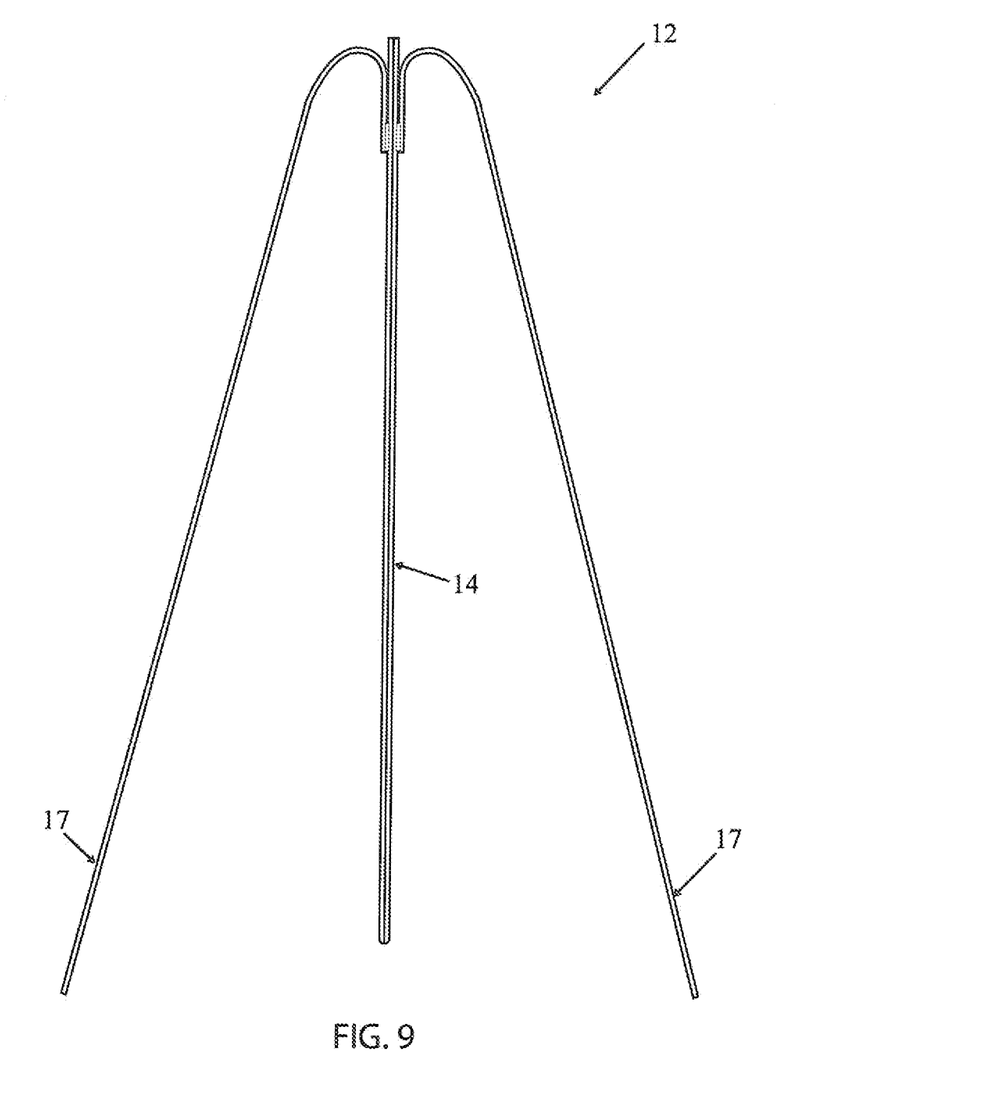
FIG. 9 is a side view of a partially constructed sheath during manufacturing according to FIG. 1.
Figure 10:
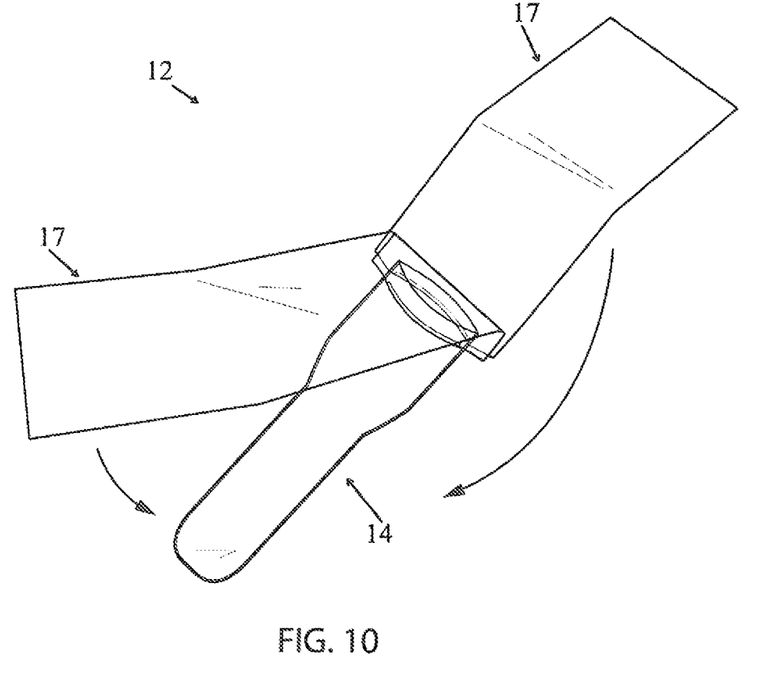
FIG. 10 is a perspective view of the sheath according to FIG. 1.

Referring to FIG. 9, the sheath according to FIG. 1 is shown in an intermediate assembly stage. The cable cover segment 16, as seen in FIG. 1, is shown prior to bonding each flap 17 to one another forming the cable cover segment 16 and encapsulating the instrument cover segment 14. As shown in FIG. 10, each flap 17 is folded over in order to encase the outside of the instrument cover section 14. The sides of the flaps 17 may then be fused together forming the sheath 12 as shown in FIG. 1, while not fusing the ends of the flap together, allowing the completed cable cover segment 16 to unfold over the cable of a probe tip 30, as partially seen in FIG. 3.

Although the best mode contemplated by the inventors of carrying out the present invention is disclosed above, practice of the present invention is not limited thereto. It will be manifest that various additions, modifications, and rearrangements of the aspects and features of the present invention may be made in addition to those described above without deviating from the spirit and scope of the underlying inventive concept. The scope of some of these changes is discussed above. The scope of other changes to the described embodiments that fall within the present invention but that are not specifically discussed above will become apparent from the appended claims and other attachments.

We claim:
1. A sheath comprising:
a sleeve layer defining an instrument cover segment;

an outer layer defining a cable cover segment, the outer layer including a pair of flaps folded over the instrument cover segment; and an adhesive layer on at least one of the pair of flaps;

wherein the outer layer and sleeve layer comprise a pre-use configuration in which the sleeve layer is configured to receive a portion of an instrument and the outer layer overlies at least a portion of the instrument cover segment, and wherein the outer layer and the sleeve layer are convertible from the pre-use configuration to an in-use configuration wherein the cable cover segment extends longitudinally with respect to the instrument cover segment and wherein the adhesive layer adheres the pair or flaps together about the instrument.

2. The sheath of claim 1, wherein the instrument cover segment includes a tip end configured for receiving a tip of the instrument and an opposite outer end, the cable cover segment defining an inner end connected to the outer end of the instrument cover segment.

3. The sheath of claim 2, wherein the cable cover segment defines an outer end arranged relatively closer to the tip end of the instrument cover segment when the sheath is in the pre-use configuration and relatively further from the tip end of the instrument cover segment when the sheath is in the in-use configuration.

4. The sheath of claim 3, wherein the outer end of the cable cover segment travels longitudinally past and concentrically outward of the inner end of the cable cover segment while the cable cover segment inverts when the outer layer and sleeve layer are converted from the pre-use configuration to the in-use configuration.

5. The sheath of claim 1, wherein a fold is defined between the instrument and cable cover segments when the sheath is in the pre-use configuration.

6. The sheath of claim 5, wherein the sleeve layer defines a pocket for receiving the instrument and the outer layer is arranged outwardly of and covering the sleeve layer in the pre-use configuration.

7. The sheath of claim 6, wherein the outer layer is configured to be pulled down over a cable of the instrument.

8. The sheath of claim 7, wherein a tab defines a paper layer arranged between at least one of the outer and sleeve layers.

9. The sheath of claim 7, wherein pulling the outer layer toward the fold inverts the cable cover segment from the pre-use configuration to the in-use configuration during an installation of the sheath upon the instrument.

10. The sheath of claim 9, wherein the instrument cover segment includes a tip end receiving a tip of the instrument and an opposite outer end, the cable cover segment defining an inner end connected to the outer end of the instrument cover segment at the fold when the sheath is in the pre-use configuration.

11. The sheath of claim 10, wherein during installation of the sheath upon the instrument, the fold travels along the length of the cable cover segment toward an open end of the cable cover segment such that the cable cover segment inverts during an installation of the sheath upon the instrument by pulling the cable cover over the instrument and onto a cable or tube of the instrument.

12. The sheath of claim 11, wherein each of the flaps of the outer layer is connected to the sleeve layer by a weld.

13. The sheath of claim 11, wherein a fold is defined between the instrument cover segment and each of the flaps of the cable cover segment when the sheath is in the pre-use configuration.

14. A sheath configured for receiving a tip of an instrument comprising:
an outer layer with a pair of flaps for adjusting the sheath about the instrument;
a generally tubular sleeve layer coupled to the outer layer defining an instrument cover segment;
a paper layer connected to the outer layer and sleeve layer;
a tab at one end of the paper layer to remove the paper layer from the outer layer and the sleeve layer once the sleeve layer covers a portion of the instrument; and
an adhesive layer on at least one of the pair of flaps for adhering the flaps about the instrument.

15. The sheath of claim 14 wherein the outer layer defines a cable cover segment and wherein said outer layer and sleeve layer comprise a pre-use configuration in which the sleeve layer is configured to receive a portion of an instrument and the outer layer overlies at least a portion of the instrument cover segment and wherein the outer layer and the sleeve layer are convertible from the pre-use configuration to an in-use configuration wherein the cable cover segment extends longitudinally with respect to the instrument cover segment.

16. The sheath of claim 14 wherein the sleeve layer is coupled to the paper layer by welds.

17. The sheath of claim 14 wherein the sleeve layer is constructed of a polymeric material.

18. A sheath comprising:
an outer layer; and
a sleeve layer defining an instrument cover segment;
a tip end on the instrument cover segment configured for receiving a tip of an instrument;
an outer end on the instrument cover segment opposite the tip end;
a tab defining a paper layer releasably connected to the outer layer and sleeve layer;
wherein the outer layer and sleeve layer comprise a pre-use configuration in which the sleeve layer is configured to receive a portion of an instrument and the outer layer overlies at least a portion of the instrument cover segment and wherein the outer layer and the sleeve layer are convertible from the pre-use configuration to an in-use configuration wherein the outer layer extends longitudinally with respect to the instrument cover segment; and
wherein in the pre-use configuration, the outer layer includes a pair of flaps with at least one flap folded over the instrument cover segment and wherein in the in-use configuration, the flaps are configured for securing to each other so as to provide a continuous barrier extending the entire length of the instrument.

* * * * *